US012605329B2

(12) United States Patent
Resch et al.

(10) Patent No.: US 12,605,329 B2
(45) Date of Patent: Apr. 21, 2026

(54) CLEANSING PREPARATION CONTAINING CAESALPINIA SPINOSA GUM

(71) Applicant: BEIERSDORF AG, Hamburg (DE)

(72) Inventors: Benedict Resch, Hamburg (DE); Denise Gritza, Hamburg (DE); Eefje Koop, Norderstedt (DE)

(73) Assignee: BEIERSDORF AG, Hamburg (DE)

( * ) Notice: Subject to any disclaimer, the term of this patent is extended or adjusted under 35 U.S.C. 154(b) by 466 days.

(21) Appl. No.: 17/754,656

(22) PCT Filed: Aug. 4, 2020

(86) PCT No.: PCT/EP2020/071870

§ 371 (c)(1),
(2) Date: Apr. 8, 2022

(87) PCT Pub. No.: WO2021/069126

PCT Pub. Date: Apr. 15, 2021

(65) Prior Publication Data

US 2024/0091130 A1 Mar. 21, 2024

(30) Foreign Application Priority Data

Oct. 11, 2019 (DE) ........................ 102019215615.0

(51) Int. Cl.
*A61K 8/9789* (2017.01)
*A61Q 19/10* (2006.01)

(52) U.S. Cl.
CPC ............ *A61K 8/9789* (2017.08); *A61Q 19/10* (2013.01); *A61K 2800/48* (2013.01); *A61K 2800/596* (2013.01)

(58) Field of Classification Search
CPC .............. A61K 8/9789; A61K 2800/48; A61K 2800/596; A61Q 19/10
See application file for complete search history.

(56) References Cited

U.S. PATENT DOCUMENTS

2007/0269397 A1* 11/2007 Terada ..................... A61Q 5/02 424/70.13
2009/0258806 A1* 10/2009 Hoffmann ................ A61K 8/33 510/122
2014/0228268 A1 8/2014 Fahl et al.
2019/0365623 A1* 12/2019 Botto ..................... A61K 8/817

FOREIGN PATENT DOCUMENTS

DE 102011084888 A1 4/2013
DE 102014225009 A1 6/2016
DE 102017217306 A1 3/2019
EP 1647591 A1 4/2006
WO 2019185915 A1 10/2019

OTHER PUBLICATIONS

Anonymous, "Hair & Body Shower Gel", GNPD, MINTEL, (Jul. 17, 2019), Database accession No. 6717789, URL: www.gnpd.com.
Anonymous, "Natural Soap No.1", GNPD, MINTEL, (May 30, 2019), Database accession No. 6584021, URL: www.gnpd.com.
Anonymous, "Sport 2 in 1 Hair & Body Wash", GNPD, MINTEL, (Mar. 1, 2019), Database accession No. 6373327, URL: www.gnpd.com.
Anonymous, "Regenerating Body Wash", GNPD, MINTEL, (Aug. 22, 2019), Database accession No. 6807057, URL: www.gnpd.com.
Nn, "Tara gum, a safe and natural alternative to guar gum", (Jul. 10, 2019), pp. 1-4, URL: https://web.archive.org/web/20190710020718/https://www.silvateam.com/en/products-and-services/food-ingredients/tara-gum/tara-gum-safe-and-natural-alternative-guar-gum.html, (Oct. 12, 2020).
Anonymous, "3-in-1 Refreshing Shampoo and Shower Gel", GNPD, MINTEL, Dec. 2015, Database accession No. 3639133, URL: www.gnpd.com.
Seppic: Solagum Tara www.seppic.com May 7, 2020.

* cited by examiner

*Primary Examiner* — Jennifer A Berrios
*Assistant Examiner* — Chasity P Janosko
(74) *Attorney, Agent, or Firm* — Abel Schillinger, LLP

(57) ABSTRACT

The present invention relates to a cosmetic cleansing preparation containing *Caesalpinia spinosa* gum.

20 Claims, No Drawings

CLEANSING PREPARATION CONTAINING CAESALPINIA SPINOSA GUM

BACKGROUND OF THE INVENTION

1. Field of the Invention

The present invention relates to an acrylate-free cosmetic cleansing preparation.

2. Discussion of Background Information

In general, cosmetic products are not only used for looking beautiful and attractive, but their effect makes a decisive contribution to increased self-esteem and the well-being of people. Accordingly, a wide variety of cosmetic products are used for daily cleansing and care of human skin.

The main purpose of daily body cleansing with shower gels is to effectively remove sweat residues, grease, deposited dirt particles and dead skin residues from the skin. Shower gels generally contain anionic surfactants, which enable particularly effective cleansing. Furthermore, cleansing products of this type often contain other additional surfactants selected from the group of non-ionic and amphoteric surfactants.

In addition to the cleansing effect, the focus is on other product features that are relevant for use by the consumer. For instance, cleansing preparations for use in the shower should meet the following parameters:

Sensory Properties when Spread on Wet Skin:

- the product itself is very slippery when the product is rubbed between fingers and the body surface to be applied
- not stringy during spreading
- little effort required when spreading on the skin, or slight adhesion of the product to the skin
- uniform spreadability when applied Sensory Properties During and after Lathering:

- the formation of voluminous foam
- the formation of large air bubbles during lathering Sensory Properties During or after Rinsing with Water:

- rapid and easy rinseability with water after application
- no sticky residues after rinsing with water
- smooth feeling on the skin when the hand is rubbed over the skin surface which has been rinsed with water.

Such sensory properties can usually be best evaluated by means of studies with volunteers, in which the product properties are evaluated using a standardized protocol.

The sensory properties during spreading can be analyzed by first cleaning a selected skin area (e.g., pulse height) with water, applying 0.5 ml of the cleansing product to the wetted skin, moistening the area again and finally spreading the cleansing product in circular movements by finger. In this process, the first circular movement initially serves to generate a product film. If several circular movements are necessary to produce the film, the spreadability is poorer. At the same time, the extent to which force must be applied to generate a product film is assessed. As soon as a first film has formed, it is possible to assess the slipperiness of the product itself with the next circular movements with the finger, since the product should now slide particularly easily over the product film previously formed. Thus, the term "slipperiness" refers to the slip properties of the product on a product film present on the skin. Another aspect evaluated when spreading product in a circular fashion is to what extent the product is stringy during spreading.

The sensory properties of the cleansing product during lathering can be analyzed by applying a specified amount of the product to a test area on the forearm moistened with water. The area is then rubbed several times with a wet palm of the hand and the applied product is thus lathered. After a specified number of movements, the foam formed is assessed, with the total foam volume and the bubble size being the parameters to be determined.

The sensory properties during or after rinsing with water can be analyzed by holding the skin area with the previously lathered product horizontally under water and rinsing off the foam with the palm of the hand at the specified rate. During this procedure, it is possible to assess how quickly the foam can be rinsed off. At the same time, the degree of friction exerted by the palm of the hand provides a way of assessing how easily the product can be rinsed off. After rinsing, the stickiness of the residues and the smoothness of the skin can be determined by stroking the cleansed area with the hand.

Conventional cleansing preparations for skin cleansing in the shower are widely known, inter alia, from EP1647591 A1. The cleansing preparations typically contain anionic and amphoteric surfactants, a thickening polymer based on homo- or copolymers of acrylic acid and usually at least one additional agent which, among other aspects, increases the slipperiness of the preparation after the first film has formed on the skin.

However, consumers increasingly prefer cleansing preparations that do not contain homo- or copolymers of acrylic acid, since their environmental degradability is currently under discussion. Problematic here is the fact that cleansing preparations for use in the shower without homo- or copolymers of acrylic acid often do not have the slipperiness desired by the consumer when applied to wet skin.

Consequently, it was an object of the present invention to provide cleansing preparations which, without the use of homopolymers and copolymers of acrylic acid, have increased slipperiness when the cleansing preparation is applied to wet skin and a first film of components of the cleansing preparation has formed on the skin. Accordingly, the cleansing preparation should feel particularly slippery when it is spread on the skin or on the film formed on the skin by the cleansing preparation.

Surprisingly, it has now been found that the requirements could be met by the present invention.

SUMMARY OF THE INVENTION

The invention provides a cosmetic cleansing preparation for use in the shower comprising, based on the total weight of the preparation, a) 0.5 to 8% by weight anionic and/or non-ionic surfactants, b) 2.5 to 7% by weight amphoteric and/or zwitterionic surfactants, and c) *Caesalpinia spinosa* gum, characterized in that no homopolymers or copolymers of acrylic acid are present.

If weight percentages (% by weight) are stated below without reference to a specific composition or specific mixture, these figures always relate to the total weight of the cosmetic cleansing preparation. If ratios of components/substances/groups of substances are disclosed below, these ratios relate to the ratios by weight of the components/substances/groups of substances cited.

The phrases "according to the invention", "advantageous according to the invention", "advantageous in the context of the present invention" etc., always refer in the context of the present disclosure both to the preparation according to the invention and to the use according to the invention and the process according to the invention.

Unless otherwise stated, all tests were carried out under standard conditions. The phrase "standard conditions" signifies 20° C., 1013 hPa and a relative humidity of 50%.

Anionic surfactants generally have carboxylate, phosphate, sulfate or sulfonate groups as functional groups. In aqueous solution, in an acidic or neutral medium, they form negatively charged organic ions.

Anionic surfactants that may be used advantageously according to the invention are sulfuric acid esters, such as

- alkyl ether sulfate, in particular lauryl ether sulfates of sodium, ammonium, magnesium, MIPA and TIPA, sodium myristyl ether sulfate and the substance known under the INCI name as sodium C12-13 pareth sulfate;
- alkyl sulfates, in particular sodium, ammonium and TEA lauryl sulfate;

and sulfonic acids and salts, such as

- acyl isethionates, in particular sodium/ammonium cocoyl isethionate;
- alkylaryl sulfonates;
- alkyl sulfonates, in particular sodium cocomonoglyceride sulfate, sodium C12-14 olefin sulfonate, sodium lauryl sulfoacetate and magnesium PEG-3 cocamide sulfate,
- sulfosuccinates, in particular dioctyl sodium sulfosuccinate, disodium laureth sulfosuccinate, disodium lauryl sulfosuccinate, disodium undecylenamido MEA-sulfosuccinate and PEG-5 lauryl citrate sulfosuccinate;

Other anionic surfactants that may be used advantageously are acylamino acids and salts thereof, such as

- acyl glutamates, in particular sodium acyl glutamate, di-TEA-palmitoyl aspartate and sodium caprylic/capric glutamate;
- acyl peptides, in particular palmitoyl hydrolyzed milk protein, sodium cocoyl hydrolyzed soy protein and sodium/potassium cocoyl hydrolyzed collagen,
- acyl sarcosinates, in particular myristoyl sarcosine, TEA-lauroyl sarcosinate, sodium lauroyl sarcosinate and sodium cocoyl sarcosinate;
- acyl taurates, in particular sodium lauroyl taurate and sodium methyl cocoyl taurate;
- acyl lactylates, in particular lauroyl lactylate, caproyl lactylate;
- acyl alaninates;
- acyl glycinates, in particular sodium cocoyl glycinate.

Further anionic surfactants that may be used advantageously are the groups of carboxylic acids and carboxylic acid derivatives specified below:

- carboxylic acids, in particular lauric acid, aluminum stearate, magnesium alkoxide and zinc undecylenate;
- ester carboxylic acids such as calcium stearoyl lactylate, laureth-6 citrate and sodium PEG-4 lauramide carboxylate;
- ether carboxylic acids such as sodium laureth-13 carboxylate and sodium PEG-6 cocamide carboxylate;

and phosphoric acid esters and salts such as DEA oleth-10 phosphate and dilaureth-4 phosphate.

It is particularly advantageous if the cosmetic cleansing preparation according to the invention contains one or more anionic surfactants according to the formula (I)

$$RO—(CH_2CH_2O)_x—(CH_2—CHR^1O)_y—(CH_2CH_2O)_z—SO_3^-M^+ \quad (I)$$

characterized in that

- R is a linear or branched $C_8$-$C_{18}$-alkyl radical or mixtures of different linear or branched $C_8$-$C_{18}$-alkyl radicals;
- $R^1$ is methyl, ethyl or mixtures thereof;
- $M^+$ is a cation, selected from the group consisting of alkali metals, $NH_4^+$ and $HNR^2_3{}^+$, wherein $R^2$ is selected from the group consisting of linear or branched alkyl radicals, $CH_2CH_2OH$ and $CH_2CH(OH)CH_3$;
- x is an integer in the range of 0-3;
- y is an integer in the range of 0-10; and
- z is an integer in the range of 0-30.

Particularly preferred surfactants of the formula (I) are selected from the group of sodium laureth sulfate (sodium lauryl ether sulfate) and/or ammonium laureth sulfate (ammonium lauryl ether sulfate). If the cosmetic preparation according to the invention comprises an anionic surfactant according to the formula (I), preferably sodium laureth sulfate (sodium lauryl ether sulfate) and/or ammonium laureth sulfate (ammonium lauryl ether sulfate), then it is preferred if the proportion of these anionic surfactants is from 0.5% by weight to 8% by weight, preferably from 2% by weight to 7.5% by weight and particularly preferably from 4% by weight to 7% by weight, based on the total weight of the cosmetic preparation.

Particularly advantageously present are sodium laureth sulfate (sodium lauryl ether sulfate) and/or ammonium laureth sulfate at a proportion of from 0.5% by weight to 8% by weight, preferably from 2% by weight to 7.5% by weight and particularly preferably from 4% by weight to 7% by weight, based on the total weight of the cosmetic preparation. It is particularly advantageous if, apart from sodium laureth sulfate, no other anionic surfactants are present. Embodiments which are intended to deliver a particularly effective cleansing performance are advantageously characterized in that anionic surfactants are present and non-ionic surfactants are omitted.

If non-ionic surfactants are present, these are advantageously selected from the group of:

- fatty acid alkanolamides of the general formula (II)

(II)

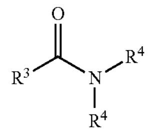

- where $R^3$ is a linear or branched, saturated or unsaturated alkyl or alkenyl radical having 8 to 24 carbon atoms, $R^4$ is each a hydrogen atom or a $—(CH_2)_nOH$ group, in which n can be 2 or 3, with the proviso that at least one of the $R^4$ groups is a $—(CH_2)_nOH$ group, for example cocamide MEA/DEA/MIPA;
- addition products of ethylene oxide onto fatty acid alkanolamides
- $C_8$-$C_{30}$-fatty acid mono- and/or diesters of addition products of 1 to 50 mol of ethylene oxide onto glycerol;
- addition products of 2 to 50 mol of ethylene oxide and/or 0 to 5 mol of propylene oxide onto linear or branched fatty alcohols having 8 to 30 carbon atoms, onto fatty acids having 8 to 30 carbon atoms and onto alkylphenols having 8 to 15 carbon atoms in the alkyl group; and
- alkyl polyglycosides, such as preferably lauryl glycoside, decyl glycoside and coco glycoside.

Advantageous embodiments of the invention are characterized in that these comprise alkyl glycosides, especially decyl glycoside and/or coco glycoside, as non-ionic surfactants. If the cosmetic cleansing preparation according to the invention comprises alkyl glycosides, especially decyl glycoside and/or coco glycoside, it is preferred if the proportion of alkyl glycosides is from 0.5% by weight to 5% by weight and preferably from 2% by weight to 4% by weight, based on the total weight of the cleansing preparation.

Foaming of the cleansing preparation is promoted by using the non-ionic surfactants according to the invention, in particular by using the non-ionic surfactants at a total proportion of from 0.1% by weight to 5% by weight, based on the total weight of the cleansing preparation. In addition, such use of non-ionic surfactants makes it possible to increase the viscosity of the cleansing preparation. Within these embodiments, it is also preferred if no anionic surfactants are present. Accordingly, the cleansing preparations are particularly mild on the skin.

Furthermore, the cosmetic cleansing preparation according to the invention comprises one or more amphoteric and/or zwitterionic surfactants. Amphoteric and/or zwitterionic surfactants that may be used advantageously are

- acyl-/dialkylethylenediamine, in particular sodium acylamphoacetate, disodium acylamphodipropionate, disodium alkylamphodiacetate, disodium cocoamphodiacetate, sodium cocoamphomonoacetate, sodium acylamphohydroxypropylsulfonate, disodium acylamphodiacetate and sodium acylamphopropionate;
- N-alkylamino acids, in particular aminopropylalkylglutamide, alkylaminopropionic acid, sodium alkylimidodipropionate and lauroamphocarboxyglycinate;
- betaines, in particular coco betaine, cocoamidopropyl betaine; and
- sultaines, in particular lauryl hydroxysultaine.

Particularly advantageously present are the amphoteric and/or zwitterionic surfactants known by the INCI names sodium cocoamphoacetate, disodium cocoamphodiacetate, sodium cocoamphopropionate, disodium cocoamphodipropionate, coco betaine, lauryl betaine and/or cocamidopropyl betaine. From the above group, cocamidopropyl betaine is selected as the most preferred amphoteric and/or zwitterionic surfactant.

The proportion of the amphoteric and/or zwitterionic surfactants, in particular the amphoteric and/or zwitterionic surfactants listed above as particularly advantageous, in the cosmetic cleansing preparation according to the invention is advantageously from 2.5 to 7% by weight, preferably from 3% by weight to 6% by weight and particularly preferably from 3.5% by weight to 5.5% by weight, based on the total weight of the cleansing preparation.

Advantageous embodiments of the invention are therefore characterized in that cocamidopropyl betaine is present in the cosmetic cleansing preparation according to the invention at a proportion of from 2.5 to 7% by weight, preferably from 3% by weight to 6% by weight and particularly preferably from 3.5% by weight to 5.5% by weight, based on the total weight of the cleansing preparation. Within these embodiments, it is also particularly preferred if no other amphoteric and/or zwitterionic surfactants are present besides cocamidopropyl betaine.

According to the invention, the cosmetic cleansing preparation comprises *Caesalpinia spinosa* gum. It is particularly advantageous if the proportion of *Caesalpinia spinosa* gum is from 0.1 to 1% by weight, preferably from 0.15 to 0.46% by weight and particularly preferably from 0.2 to 0.4% by weight, based on the total weight of the preparation.

It was extremely surprising to those skilled in the art that even with the addition of small fractions of *Caesalpinia spinosa* gum of up to 0.4% by weight, a significant increase with respect to slipperiness, as described above, can already be produced. Other polymers that could be used to increase slipperiness usually require higher use concentrations. As a result, there is usually a significantly increased viscosity in the preparation. Surprisingly, however, it has now been found that by using the invention, preparations having a lower viscosity and high slipperiness, as described above, can be obtained. The preparations can thus be used much more flexibly, since less viscous cleansing preparations for use in the shower are also obtained. For example, removal via a pump dispenser is possible.

According to the present invention, it is advantageous in some embodiments if no other natural polymeric thickeners are present in addition to *Caesalpinia spinosa* gum.

Other advantageous embodiments of the invention are characterized in that these additionally comprise xanthan gum to adjust the viscosity of the preparation. If xanthan gum is present, the total proportion of xanthan gum is preferably from 0.01 to 0.3% by weight, based on the total weight of the cleansing preparation.

*Caesalpinia spinosa* gum is a non-ionic polysaccharide in the form of powder. It is commercially available from Seppic under the trade name SOLAGUM™ TARA.

Furthermore, it is advantageous in the context of the present invention if the preparation comprises PEG-7 glyceryl cocoate.

The total proportion of PEG-7 glyceryl cocoate in the cosmetic cleansing preparation is advantageously selected from 0.2% by weight to 5% by weight, preferably from 0.5% by weight to 2.5% by weight and particularly preferably from 1% by weight to 2% by weight, based on the total weight of the cleansing composition.

It is also advantageous according to the invention if PEG-200 hydrogenated glyceryl palmate, PEG-40 hydrogenated castor oil and/or PEG-90 glyceryl isostearate are also present. It is advantageous in this case if the proportion of PEG-200 hydrogenated glyceryl palmate, PEG-40 hydrogenated castor oil and/or PEG-90 glyceryl isostearate is from 0.1% by weight to 1.5% by weight, preferably from 0.2% by weight to 1.3% by weight, particularly preferably from 0.5% by weight to 1% by weight, based on the total weight of the cleansing preparation. It is particularly advantageous if at least PEG-40 hydrogenated castor oil is present at a proportion of from 0.1% by weight to 1.5% by weight, preferably from 0.2% by weight to 1.3% by weight, particularly preferably from 0.5% by weight to 1% by weight, based on the total weight of the cleansing preparation.

Furthermore, it is advantageous if the cosmetic cleansing preparations according to the present invention comprise water as the cosmetic carrier, with water being present at a proportion of from 70% by weight to 92% by weight, preferably from 75% by weight to 90% by weight and particularly preferably from 80% by weight to 88% by weight, based on the total weight of the cleansing preparation.

It is also advantageous in the context of the present invention if the preparation is free from silicone oils.

Preservatives commonly used in cosmetics may be used to preserve the present cosmetic cleansing preparations. These include, for example, parabens such as methylparaben, propylparaben, ethylparaben and butylparaben. However, the use of acid-based preservatives, which are used in the food industry, is also desirable. These include, for example, benzoic acid and/or salicylic acid and/or salts thereof. It is particularly preferred if sodium benzoate is present, wherein the proportion of sodium benzoate is preferably in the range from 0.2 to 0.65% by weight, based on the total weight of the preparation.

Furthermore, it has proven to be advantageous if the preparation comprises at least citric acid or salts thereof. If citric acid or salts thereof are present, it is advantageous if the proportion of these components is from 0.2 to 1% by weight, based on the total weight of the cleansing preparation.

The cleansing preparation of the invention is advantageously characterized in that under standard conditions it has a viscosity of less than 10,000 mPa·s, more preferably less than 5,000 mPa·s, more preferably less than 4,000 mPa·s and particularly preferably less than 3,500 mPa·s. Furthermore, it is advantageous if the cosmetic preparation has a viscosity of at least 500 mPa·s, preferably at least 1,500 mPa·s, more preferably at least 2,000 mPa·s and particularly preferably at least 2,300 mPa·s. Accordingly, the viscosity of the cosmetic preparation is advantageously 500 to 10,000 mPa·s, preferably 1,500 to 5,000 mPa·s, more preferably 2,000 to 4,000 mPa·s and particularly preferably 2,300 mPa·s to 3,500 mPa·s.

Where viscosity values are specified in this disclosure, all values refer to measurement at 25° C. in a 150 ml wide-necked flask (VWR No.: 807-001) using a Rheomat R 123 from proRheo. The Rheomat R 123 from proRheo GmbH is a rotational viscometer, i.e. a measuring bob rotates in the substance to be measured. The force required to rotate the measuring bob in the sample at a specified speed is measured. The viscosity is calculated from this torque, the rotational speed of the measuring bob and the geometric dimensions of the measuring system used. The measuring bob used is measuring bob No. 1 (article No. 200 0191), suitable for a viscosity range of up to 10 000 [mPa·s], speed range 62.5 $min^{-1}$. Unless stated otherwise, the viscosity is always measured 24 hours after the preparation has been prepared.

Furthermore, advantageous embodiments of the invention are characterized in that the total proportion of all surfactants present is at most 14% by weight, preferably at most 13.5% by weight and especially at most 12.5% by weight, where the figures refer to the total weight of the cosmetic cleansing preparation.

Furthermore, the cosmetic cleansing preparation according to the invention advantageously comprises at least one natural oil. Natural oils are understood to mean all oils of vegetable and animal origin. It is particularly preferred that only oils of vegetable origin are used as natural oils.

Among the advantageous natural oils according to the invention are the natural oils selected from the group of sunflower oil (*Helianthus annuus* seed oil), rapeseed oil (*Canola* oil), soybean oil (*Glycine soja* oil), olive oil (*Olea europaea* fruit oil), almond oil (*Prunus amygdalus dulcis* oil), avocado oil (*Persea gratissima* oil), walnut oil (*Juglans regia* seed oil), peach kernel oil (*Prunus persica* kernel oil), apricot kernel oil (*Prunus armeniaca* kernel oil), sesame oil (*Sesamum indicum* seed oil), *camellia* oil (*Camellia oleifera/Camellia sasanqua*), evening primrose oil (*Oenothera biennis*), *macadamia* nut oil (*Macadamia* intergrifolia seed oil), thistle oil (*Silybum marianum* seed oil), wheat germ oil (*Triticum vulgare* germ oil), palm kernel oil (*Elaeis guineensis* kernel oil), palm oil (*Elaeis guineensis* oil), grape seed oil (*Vitis vinifera* seed oil), argan oil (*Argania spinosa* seed oil), peanut oil (*Arachis hypogaea* oil), pumpkin seed oil (*Cucurbita pepo* seed oil), castor oil (*Ricinus communis* seed oil), rice bran oil (*Oryza sativa* bran oil), vegetable oil (*Olus* oil) and mixtures of these oils.

The use of vegetable oils is preferred over animal oils; in particular the natural oils selected from the group of soybean oil (*Glycine soja* oil), sunflower oil (*Helianthus annuus* seed oil), rapeseed oil (*Canola* oil) and olive oil (*Olea europaea* fruit oil) are present in the cosmetic cleansing preparation.

Furthermore, it is preferred if the natural oils are advantageously present at a proportion of at least 0.05% by weight, preferably at least 0.1% by weight, more preferably at least 0.2% by weight, more preferably at least 0.3% by weight, more preferably at least 0.4% by weight, more preferably at least 0.5% by weight, more preferably at least 0.6% by weight and particularly preferably at least 0.7% by weight, based on the total weight of the preparation.

Advantageously according to the invention, the cleansing preparation advantageously comprises sodium chloride. If sodium chloride is present, the proportion of sodium chloride is advantageously from 0.15 to 1.2% by weight and particularly advantageously from 0.6 to 1% by weight, based on the total weight of the preparation.

The cleansing preparations according to the invention may advantageously contain opacifiers. Opacifiers are water-insoluble, mostly microparticulate substances which reflect light particularly well and impart a milky or cloudy appearance to the cleansing preparations. Opacifiers according to the invention are glycol distearate, glyceryl stearate or PEG-3 distearate.

Furthermore, the cleansing preparations according to the invention may comprise further substances selected from the group of glycerol, propanediol and sorbitol.

The cosmetic preparation according to the invention may also comprise other cosmetic auxiliaries and active ingredients as are commonly used in such preparations, e.g. other active ingredients, preservatives, preservative aids, bactericides, dyes and color pigments, thickeners, moistening and/or moisturizing substances or other usual components of a cosmetic or dermatological formulation such as further polyols, foam stabilizers, organic solvents or silicone derivatives, provided that the additive does not impair or exclude the required properties with regard to stability.

DETAILED DESCRIPTION OF EXEMPLARY EMBODIMENTS OF THE INVENTION

Comparative Tests and Examples

The following examples are intended to illustrate the present invention without restricting it. Unless otherwise stated, all amounts, proportions and percentages are based on the weight and the total amount or on the total weight of the preparations.

The following formulations were prepared. The formulations Comp.1 and Comp.2 are not inventive, whereas Ex.1 is according to the invention:

| Ingredients | Comp. 1 | Comp. 2 | Ex. 1 |
|---|---|---|---|
| Sodium Laureth Sulfate | 6.51 | 6.51 | 6.51 |
| Cocamidopropyl Betaine | 4.51 | 4.51 | 4.51 |
| Glycerin | 0.4 | 0.4 | 0.4 |
| Sodium Chloride | 0.8 | 0.8 | 0.8 |
| PEG-40 Hydrogenated Castor Oil | 0.5 | 0.5 | 0.5 |
| PEG-7 Glyceryl Cocoate | 1.5 | 1.5 | 1.5 |
| Citric Acid | 0.55 | 0.55 | 0.55 |
| Sodium Benzoate | 0.45 | 0.45 | 0.45 |
| Parfum | 0.9 | 0.9 | 0.9 |
| Ceratonia Siliqua (Carob) Gum[1] | | 0.25 | |
| Caesalpinia Spinosa Gum[2] | | | 0.25 |
| Aqua | to 100 | to 100 | to 100 |
| Viscosity in mPa · s[3] | 1850 | 2550 | 2700 |

[1]Commercial product Genu Gum RL-200Z-CG from Rahn
[2]Commercial product SOLAGUM ™ TARA from Seppic
[3]See description for measurement method.

The cleansing preparations listed above were prepared and the properties thereof examined in a panel of experts on washing. The following procedure was applied:

Preparation:

Participants' forearms were cleansed using a standard shampoo, dried and acclimatized for 10 minutes. Then, the inner side of the forearm was held under running water for 2 seconds, and 0.5 ml of the preparation to be tested was applied to a 3 cm diameter circular area on the inner forearm. Before spreading, the spreading hand was held under running water for 2 seconds. Then the fingers were spread to allow water to drip off. The preparation was then spread with 2 fingers of the spreading hand in circular motions (5 cm in diameter) at 90 bpm (beats per minute), the slipperiness being assessed after 5 circles. A scale of values ranging from 1 to 5 is specified as a scalar, where 1 means not slippery and 5 means highly slippery.

Each preparation was analyzed 6 times by different experts. The mean values obtained for slipperiness are listed in the following table:

| Preparation | Slipperiness value measured (mean) |
|---|---|
| Comp. 1 | 1.8 |
| Comp. 2 | 2.8 |
| Ex. 1 | 3.5 |

Consequently, it has been found that the cleansing preparation according to the invention has a significantly increased slipperiness when spread on wet skin on which a film of product has formed.

| Ingredients | Ex. 2 | Ex. 3 | Ex. 4 | Ex. 5 | Ex. 6 |
|---|---|---|---|---|---|
| Sodium Laureth Sulfate | 6.3 | 6.3 | 3.15 | | |
| Cocamidopropyl Betaine | 4.5 | 3.0 | 3.5 | 5.0 | 3.0 |
| Glycerin | 0.135 | 0.09 | 0.105 | 0.15 | 0.09 |
| Sodium Chloride | 0.27 | 0.18 | 0.21 | 0.3 | 0.18 |
| Coco Glucoside | | | | 2.6 | 1.56 |
| Decyl Glucoside | | | | | 1.59 |
| PEG-40 Hydrogenated Castor Oil | 0.5 | 0.5 | 0.5 | 0.3 | 0.3 |
| Parfum | 1 | 1 | 1 | 0.5 | 0.5 |
| Sodium Benzoate | 0.5 | 0.5 | 0.55 | 0.45 | 0.5 |
| Citric Acid | 0.5 | 0.5 | 0.5 | 0.5 | 0.5 |
| Caesalpinia Spinosa Gum | 0.25 | 0.1 | 0.5 | 0.3 | 0.45 |
| Xanthan Gum | | 0.2 | | 0.1 | |
| Helianthus Annuus Seed Oil | 0.05 | 0.1 | | | |
| Aqua | to 100 | to 100 | to 100 | to 100 | to 100 |

What is claimed is:

1. A cosmetic cleansing preparation, wherein the preparation is suitable and formulated for use in the shower and comprises, based on a total weight of the preparation,
   (a) from 0.5% to 8% by weight of anionic and/or non-ionic surfactants,
   (b) from 2.5% to 7% by weight of amphoteric and/or zwitterionic surfactants, and
   (c) *Caesalpinia spinosa* gum,
   and wherein no homopolymers or copolymers of acrylic acid are present, and *Caesalpinia spinosa* gum and optionally, xanthan gum, are the only natural polymeric thickeners in the preparation.

2. The preparation of claim 1, wherein the preparation comprises one or more anionic surfactants of formula (I):

$$RO—(CH_2CH_2O)_x—(CH_2—CHR^1O)_y—(CH_2CH_2O)_z—SO_3\text{-}M^+ \quad (I)$$

wherein

R is a linear or branched $C_8$-$C_{18}$-alkyl radical or a mixture of different linear or branched $C_8$-$C_{18}$-alkyl radicals;

$R^1$ is a methyl, ethyl or a mixture thereof;

$M^+$ is a cation selected from alkali metals, $NH_{4+}$ and $HNR^2{}_3{}^+$, wherein $R^2$ is selected from linear or branched alkyl radicals, $CH_2CH_2OH$ and $CH_2CH(OH)CH_3$;

x is 0 or an integer of 1-3;

y is 0 or an integer of 1-10; and z is 0 or an integer of 1-30.

3. The preparation of claim 1, wherein the preparation comprises sodium laureth sulfate and/or ammonium laureth sulfate.

4. The preparation of claim 3, wherein no non-ionic surfactants are present.

5. The preparation of claim 1, wherein alkyl glycosides are present as non-ionic surfactants.

6. The preparation of claim 5, wherein decyl glycoside and/or coco glycoside are present.

7. The preparation of claim 6, wherein a proportion of the alkyl glycosides is from 0.5% to 5% by weight, based on a total weight of the cleansing preparation.

8. The preparation of claim 5, wherein no anionic surfactants are present.

9. The preparation of claim 1, wherein the amphoteric and/or zwitterionic surfactants comprise one or more of sodium cocoamphoacetate, disodium cocoamphodiacetate, sodium cocoamphopropionate, disodium cocoamphodipropionate, coco betaine, lauryl betaine and/or cocamidopropyl betaine.

10. The preparation of claim 9, wherein cocamidopropyl betaine is present at a concentration of from 2.5% to 7% by weight, based on a total weight of the cleansing preparation.

11. The preparation of claim 9, wherein besides cocamidopropyl betaine no other amphoteric and/or zwitterionic surfactants are present.

12. The preparation of claim 1, wherein *Caesalpinia spinosa* gum is present in a concentration of from 0.1% to 1% by weight, based on a total weight of the preparation.

13. The preparation of claim 12, wherein the concentration of *Caesalpinia spinosa* gum is from 0.2% to 0.4% by weight.

14. The preparation of claim 1, wherein the preparation comprises xanthan gum.

15. The preparation of claim 14, wherein the preparation comprises from 0.01% to 0.3% by weight of xanthan gum.

16. The preparation of claim 1, wherein no other natural polymeric thickeners are present.

17. The preparation of claim 1, wherein the preparation comprises PEG-7 glyceryl cocoate.

18. The preparation of claim 1, wherein the preparation further comprises sodium chloride.

19. The preparation of claim 1, wherein the preparation comprises PEG-200 hydrogenated glyceryl palmate, PEG-40 hydrogenated castor oil and/or PEG-90 glyceryl isostearate.

20. The preparation of claim 19, wherein a total concentration of PEG -200 hydrogenated glyceryl palmate, PEG-40 hydrogenated castor oil and/or PEG-90 glyceryl isostearate is from 0.1% to 1.5% by weight, based on a total weight of the cleansing preparation.

* * * * *